United States Patent
Levin et al.

(10) Patent No.: US 8,758,297 B2
(45) Date of Patent: Jun. 24, 2014

(54) MEDICAL TEMPERATURE SENSORS AND RELATED SYSTEMS AND METHODS

(75) Inventors: Roland Levin, San Ramon, CA (US); Martin Joseph Crnkovich, Walnut Creek, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 142 days.

(21) Appl. No.: 13/563,948

(22) Filed: Aug. 1, 2012

(65) Prior Publication Data

US 2012/0294734 A1 Nov. 22, 2012

Related U.S. Application Data

(63) Continuation of application No. 13/094,133, filed on Apr. 26, 2011, now Pat. No. 8,353,870.

(51) Int. Cl.
  *A61M 1/14* (2006.01)
  *A61M 1/36* (2006.01)
(52) U.S. Cl.
  CPC . *A61M 1/14* (2013.01); *A61M 1/36* (2013.01); *A61M 1/367* (2013.01); *A61M 1/369* (2013.01)
  USPC .......... 604/113; 604/4.01
(58) Field of Classification Search
  CPC ......... A61M 1/14; A61M 1/36; A61M 1/369; A61M 2001/1664; A61M 2205/3626; A61M 2205/3368; A61M 1/1654; A61M 1/1664; F04B 2201/0801; F04B 2205/10; F04B 2205/11; F04B 2207/03
  USPC ............... 604/4.01, 29, 40, 42–43, 113, 901; 417/32, 292, 63; 374/100, 132–133, 374/E15.002, E13.006, E1.019
  See application file for complete search history.

(56) References Cited

U.S. PATENT DOCUMENTS

| | | |
|---|---|---|
| 3,921,622 A | 11/1975 | Cole |
| 4,068,521 A | 1/1978 | Cosentino et al. |
| 4,341,116 A | 7/1982 | Bilstad et al. |
| 4,730,493 A | 3/1988 | Lebaud et al. |
| 4,797,655 A | 1/1989 | Orndal et al. |
| 4,919,786 A | 4/1990 | Hamner et al. |
| 5,150,969 A | 9/1992 | Goldberg et al. |
| 5,167,235 A | 12/1992 | Seacord et al. |

(Continued)

FOREIGN PATENT DOCUMENTS

| | | |
|---|---|---|
| EP | 446605 | 9/1991 |
| EP | 0715859 A1 | 12/1996 |

(Continued)

OTHER PUBLICATIONS

Notification Concerning Transmittal of International Preliminary Report on Patentability for corresponding PCT Application No. PCT/US2012/034902, mailed Nov. 7, 2013, 8 pages.

(Continued)

*Primary Examiner* — Quynh-Nhu H Vu
(74) *Attorney, Agent, or Firm* — Fish & Richardson P.C.

(57) ABSTRACT

This disclosure relates to medical temperature sensors and related systems and methods. In some aspects, a sensor assembly includes a non-invasive temperature sensor to detect a temperature of a medical fluid in a medical fluid line and an ambient temperature sensor to detect an ambient air temperature.

12 Claims, 9 Drawing Sheets

(56) References Cited

U.S. PATENT DOCUMENTS

| | | |
|---|---|---|
| 5,179,862 A | 1/1993 | Lynnworth |
| 5,392,638 A | 2/1995 | Kawahara |
| 5,394,732 A | 3/1995 | Johnson et al. |
| 5,904,708 A | 5/1999 | Goedeke |
| 6,106,477 A | 8/2000 | Miesel et al. |
| 6,142,008 A | 11/2000 | Cole et al. |
| 6,515,487 B1 | 2/2003 | Dawson et al. |
| 6,622,542 B2 | 9/2003 | Derek et al. |
| 6,626,857 B1 | 9/2003 | Ohta et al. |
| 6,796,195 B2 | 9/2004 | Povey et al. |
| 6,805,672 B2 | 10/2004 | Martin et al. |
| 6,821,249 B2 | 11/2004 | Casscells, III et al. |
| 6,852,074 B1 | 2/2005 | Jorgenson et al. |
| 6,855,122 B1 * | 2/2005 | Ohta et al. .................. 604/6.13 |
| 7,047,809 B2 | 5/2006 | Cobb |
| 7,243,541 B1 | 7/2007 | Bey et al. |
| 7,340,293 B2 | 3/2008 | McQuilkin |
| 7,440,110 B2 | 10/2008 | Hjelme et al. |
| 7,481,114 B2 | 1/2009 | Lynnworth |
| 2005/0090774 A1 | 4/2005 | Tonelli et al. |
| 2005/0171475 A1 | 8/2005 | Delnevo |
| 2006/0277977 A1 | 12/2006 | Kahn et al. |
| 2008/0098798 A1 | 5/2008 | Riley et al. |
| 2008/0184784 A1 | 8/2008 | Dam |
| 2008/0232604 A1 | 9/2008 | Dufresne et al. |
| 2008/0288204 A1 | 11/2008 | Hayter et al. |
| 2009/0012447 A1 | 1/2009 | Huitt et al. |
| 2009/0044935 A1 | 2/2009 | Nutsos |
| 2009/0078047 A1 | 3/2009 | Dam |
| 2010/0229366 A1 | 9/2010 | Childers et al. |
| 2011/0009800 A1 * | 1/2011 | Dam et al. .................. 604/6.16 |
| 2011/0106466 A1 | 5/2011 | Furmanski et al. |

FOREIGN PATENT DOCUMENTS

| | | |
|---|---|---|
| EP | 1132101 A1 | 9/2001 |
| JP | 04158258 | 6/1992 |
| JP | 09178712 | 7/1997 |
| JP | 2002-333434 | 11/2002 |
| JP | 2003-043017 | 2/2003 |
| KR | 10-0157986 | 11/1998 |
| KR | 10-2002-0063001 | 7/2002 |
| KR | 10-2003-0035584 | 5/2003 |
| KR | 10-0516727 | 9/2005 |
| WO | WO 01/92867 | 12/2001 |
| WO | 2007120812 A2 | 10/2007 |

OTHER PUBLICATIONS

International Search Report and the Written Opinion of the International Search Authority from corresponding PCT Application No. PCT/US2012/034902, mailed Jul. 25, 2012, 12 pages.

* cited by examiner

Corrected Blood Temperature Lookup Table for a Given Tubing

|     | 15   | 16   | 17   | 18   | 19   | 20   | 21   | 22   | 23   | - - - - - - | 38 |
|-----|------|------|------|------|------|------|------|------|------|-------------|----|
| 33  | 33.1 | 33.2 | 33.3 | 33.4 | 33.5 | 33.6 | 33.7 | 33.8 | 33.9 |             |    |
| 34  | 34.1 | 34.2 | 34.3 | 34.4 | 34.5 | 34.6 | 34.7 | 34.8 | 34.9 |             |    |
| 35  | 35.1 | 35.3 | 35.5 | 35.7 | 35.9 |      |      |      |      |             |    |
| 36  | 36.1 | 36.2 | 36.4 | 35.6 | 36.5 | 35.8 |      |      |      |             |    |
| 37  | 37.1 | 37.2 | 37.3 | 37.4 | 37.8 |      |      |      |      |             |    |
| 38  |      |      |      |      |      |      |      |      |      |             |    |
| 39  |      |      |      |      |      |      |      |      |      |             |    |
| ⋮   |      |      |      |      |      |      |      |      |      |             |    |
| 50  |      |      |      |      |      |      |      |      |      |             |    |

Ambient Air Temperature (154) across top; row labels (156) down left; 158 along bottom; 152 label.

FIG. 5

MEDICAL TEMPERATURE SENSORS AND RELATED SYSTEMS AND METHODS

CROSS-REFERENCE TO RELATED APPLICATIONS

This application is a continuation application of and claims priority to U.S. application Ser. No. 13/094,133, filed on Apr. 26, 2011, which is incorporated by reference herein.

TECHNICAL FIELD

This disclosure relates to medical temperature sensors and related systems and methods.

BACKGROUND

Hemodialysis is a treatment used to support a patient with insufficient renal function. During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

SUMMARY

In one aspect of the invention, a method includes detecting a temperature of a medical fluid in tubing using a non-invasive fluid temperature sensor, transmitting the detected temperature of the medical fluid to a control unit, detecting a temperature of ambient air using an ambient air temperature sensor, transmitting the detected temperature of the ambient air to the control unit, and using the control unit to calculate a corrected medical fluid temperature based on the detected temperatures of the medical fluid and the ambient air.

In another aspect of the invention, a medical sensor assembly includes a housing defining a slot to retain a medical fluid line, a non-invasive fluid temperature sensor mounted to the housing, and an ambient air temperature sensor mounted to the housing. The non-invasive fluid temperature sensor is configured to detect a temperature of medical fluid in the medical fluid line when the medical fluid line is disposed in the slot and the medical fluid is flowing through the medical fluid line.

In an additional aspect of the invention, a medical fluid pumping system includes a medical fluid pumping machine including a pump and fluid circuitry including tubing that can be connected to the pump in a manner such that the pump can move a medical fluid through the tubing of the fluid circuitry. The system further includes a sensor assembly that includes a housing defining a slot to retain a portion of tubing of the fluid circuitry, a non-invasive fluid temperature sensor mounted to the housing, and an ambient air temperature sensor mounted to the housing. The non-invasive fluid temperature sensor is configured to detect a temperature of medical fluid in the portion of tubing of the fluid circuitry when the portion of tubing is disposed in the slot and the medical fluid is flowing through the portion of tubing.

Implementations can include one or more of the following features.

In some implementations, the medical fluid is blood.

In some implementations, the control unit is a control unit of a hemodialysis machine.

In some implementations, calculating the corrected medical fluid temperature includes referencing a look-up table that provides a corrected medical fluid temperature for each of multiple different combinations of detected temperatures of medical fluid and detected temperatures of ambient air.

In some implementations, calculating the corrected medical fluid temperature includes inputting the detected temperatures of the medical fluid and the ambient air into an equation to obtain the corrected medical fluid temperature.

In some implementations, calculating the corrected medical fluid temperature includes running a statistical analysis to obtain the corrected medical fluid temperature.

In some implementations, the method further includes determining multiple corrected medical fluid temperatures for multiple different combinations of medical fluid temperatures and ambient air temperatures and storing the multiple corrected medical fluid temperatures in the control unit.

In some implementations, determining the multiple corrected medical fluid temperatures includes detecting temperatures of a test fluid using an invasive temperature sensor.

In some implementations, determining the multiple corrected medical fluid temperatures further includes altering the temperature of the test fluid and ambient air during a test period.

In some implementations, the non-invasive fluid temperature sensor is an infrared sensor.

In some implementations, detecting the temperature of the medical fluid includes transmitting an infrared signal through the tubing and the medical fluid and then receiving the infrared signal.

In some implementations, the non-invasive fluid temperature sensor and the ambient air temperature sensor are mounted to a single housing.

In some implementations, the housing defines a slot configured to receive a portion of the tubing therein.

In some implementations, the non-invasive fluid temperature sensor is configured to contact the portion of the tubing when the portion of the tubing is disposed in the slot of the housing.

In some implementations, the medical fluid line is a blood line.

In some implementations, the ambient air temperature sensor is mounted to an outer surface of the housing.

In some implementations, the non-invasive fluid temperature sensor is mounted to an inner surface of the housing such that the non-invasive fluid temperature sensor is adjacent the medical fluid line when the medical fluid line is disposed in the slot.

In some implementations, the non-invasive fluid temperature sensor is positioned to contact the medical fluid line when the medical fluid line is disposed in the slot.

In some implementations, the non-invasive fluid temperature sensor is positioned in the slot in the housing.

In some implementations, the medical fluid pumping machine is a dialysis machine.

In some implementations, the medical fluid pumping machine includes a control unit that is in communication with the non-invasive fluid temperature sensor and the ambient air temperature sensor.

In some implementations, the control unit includes a look-up table that provides a corrected medical fluid temperature for each of multiple different combinations of temperatures of medical fluid detected by the non-invasive fluid temperature sensor and temperatures of ambient air detected by the ambient air temperature sensor.

In some implementations, the control unit includes an equation to obtain a corrected medical fluid temperature based on a temperature of medical fluid detected by the non-invasive fluid temperature sensor and a temperature of ambient air detected by the ambient air temperature sensor.

In some implementations, the control unit is adapted to run a statistical analysis to obtain a corrected medical fluid temperature based on a temperature of medical fluid detected by the non-invasive fluid temperature sensor and a temperature of ambient air detected by the ambient air temperature sensor.

In some implementations, the fluid circuitry further includes a drip chamber, a dialyzer system, an air release chamber, and a structural support member.

In some implementations, the non-invasive fluid temperature sensor is positioned downstream of the air release chamber.

Implementations can include one or more of the following advantages.

In some implementations, the temperature sensor assembly is configured to detect the temperature of a medical fluid (e.g., blood) flowing through the tubing and the ambient air temperature. These temperature measurements can be used to determine a corrected or more accurate medical fluid temperature reading. For example, the detected temperatures of the medical fluid and the ambient air can be transmitted to a control unit that is able to calculate or access the corrected medical fluid temperature reading. The corrected medical fluid temperature reading can be used to more accurately control the medical fluid temperature such that the medical fluid can be maintained within a desired temperature range.

In certain implementations, the medical fluid is blood being treated by a blood process machine (e.g., a hemodialysis machine). By using the corrected blood temperature readings to ensure that the temperature of the blood is maintained within a desired range, the comfort level of the patient can be increased (e.g., maximized).

In some implementations, the non-invasive, medical fluid temperature sensor and the ambient air temperature sensor are mounted to a single housing. This arrangement can reduce the overall area occupied by the sensors. In addition, by localizing the sensors to a relatively small area of the medical fluid pumping machine, the amount of wiring and associated electrical components used to operate the sensors can be reduced.

Other aspects, features, and advantages will be apparent from the description and drawings, and from the claims.

DESCRIPTION OF DRAWINGS

FIG. 5 illustrates an example of a look-up table that can be stored in a control unit of the dialysis machine of FIG. 1 and accessed to determine a corrected blood temperature reading.

DETAILED DESCRIPTION

In general, this disclosure relates to medical temperature sensors and related systems and methods. In certain aspects of the invention, a dialysis system includes a sensor assembly having a blood temperature sensor and an ambient air temperature sensor. The blood temperature measurement can be corrected based on the ambient air temperature, as measured by the ambient air temperature sensor. Using more accurate blood temperature measurements, the dialysis system can provide blood to a patient at more accurately controlled temperatures to avoid patient discomfort. Systems and methods of the type mentioned above will be discussed below in greater detail.

Figure 1:
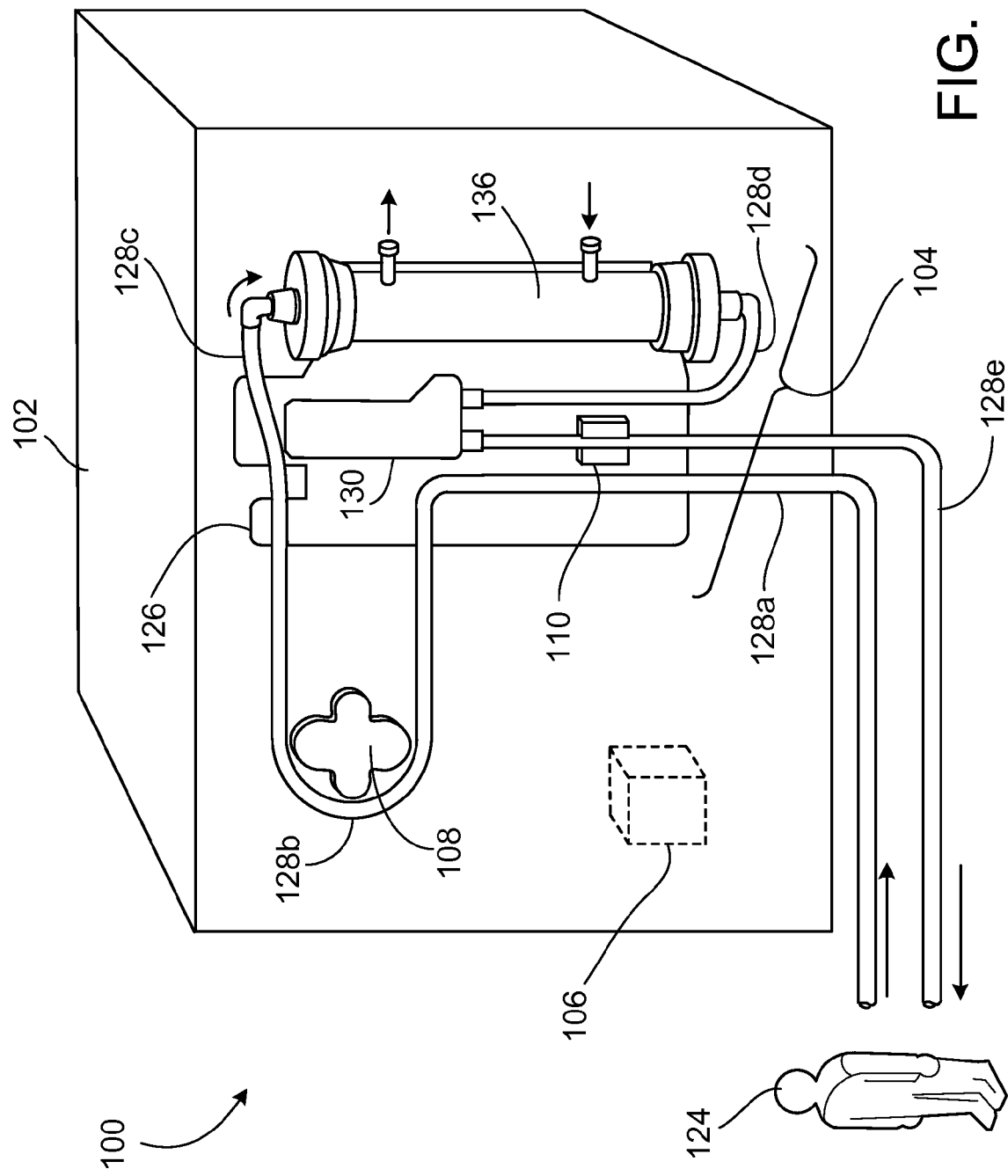
FIG. 1 is a perspective view of a dialysis system that includes a blood line set connected to the face of a hemodialysis machine.

Referring to FIG. 1, a dialysis system 100 includes a dialysis machine 102 and a disposable blood line set 104 secured to the dialysis machine 102. The dialysis machine 102 includes a dialysis machine control unit (e.g., a microprocessor) 106, a peristaltic pump 108, a blood temperature sensor assembly 110, a dialysate fluid circuit, and one or more dialysate pumps to pump dialysate through the dialysis fluid circuit. During dialysis treatment, blood is pumped through a dialyzer 136 of the blood line set 104 along with dialysate to remove impurities from the blood.

The dialysis machine control unit 106 is electrically connected to and controls the operation of various mechanical and electrical systems of the dialysis system 100. For example, the dialysis machine control unit 106 can control the operation of the peristaltic pump 108, which circulates blood through the blood line set 104, and it can monitor temperature of the blood, as detected by the blood temperature sensor assembly 110, that flows through the blood line set 104. The dialysis machine control unit 106 can also control the operation of the dialysate pump and heaters within the system to control the temperature and flow of the dialysate within the dialysate fluid circuit.

The peristaltic pump 108 is a non-invasive pump that creates flow within a loop of tubing that is disposed in a circular pump raceway by rotating a frame that has several rollers attached to the frame. As the frame rotates, the rollers compress portions of the tubing and force small pockets of fluid to flow within the loop of tubing.

Figure 2:
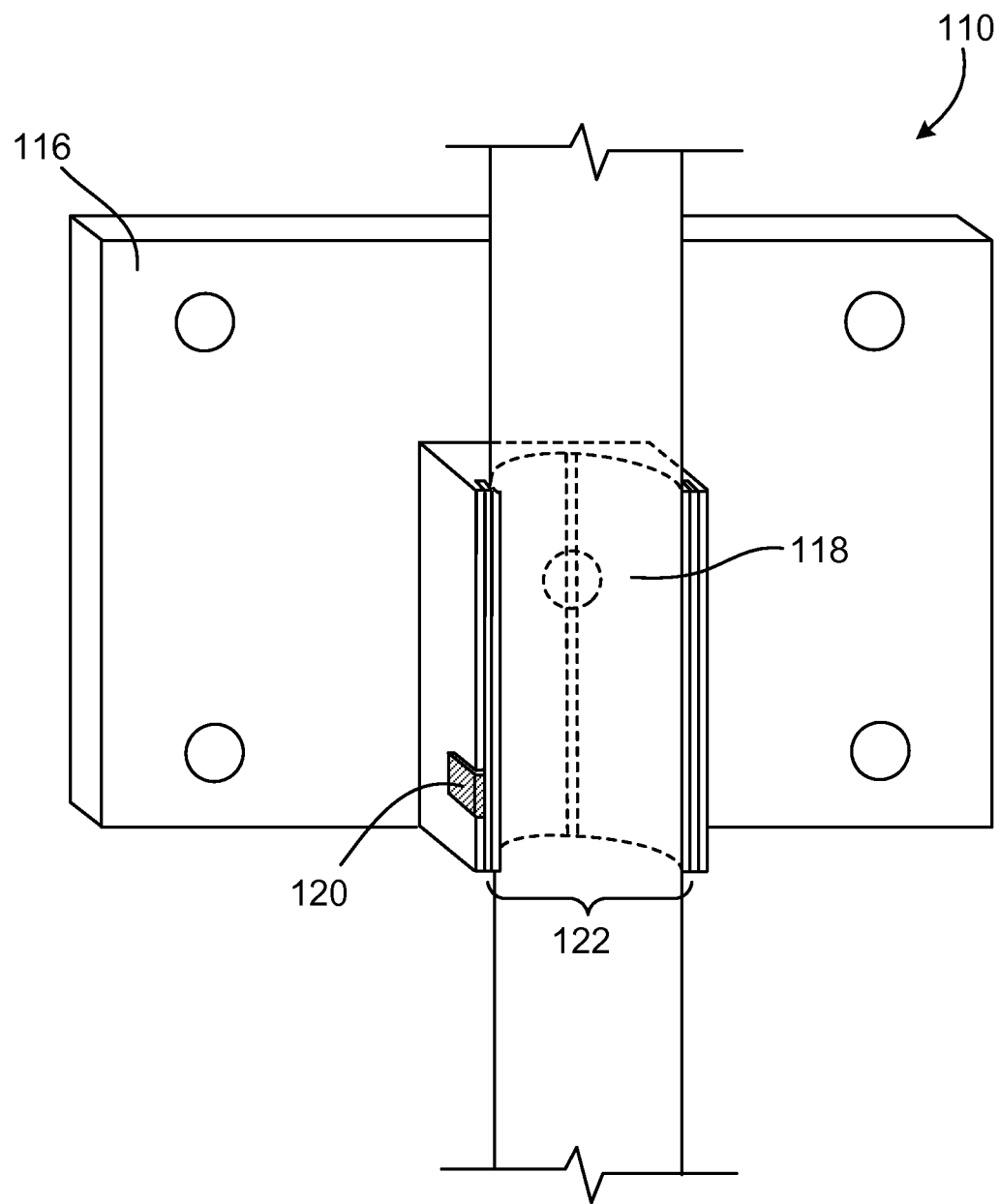
FIG. 2 is a perspective view of a temperature sensor assembly of the dialysis machine of FIG. 1 with tubing of the blood line set of FIG. 1 connected to the temperature sensor assembly.

Referring to FIG. 2, the temperature sensor assembly 110 includes a temperature sensor housing 116 to which a non-invasive blood temperature sensor 118 and an ambient air temperature sensor 120 are secured. The temperature sensor housing 116 is a molded body device that provides mounting locations for the non-invasive blood temperature sensor 118 and the ambient air temperature sensor 120. The temperature sensor housing 116 includes a tubing slot or recess 122 that has a diameter equal to or slightly less than the diameter of the dialysis system blood line tubing so that the tubing can be secured in the slot during treatment. The temperature sensor housing 116 is typically large enough to provide sufficient surface area for temperature sensors 118, 120 to be mounted thereto, but small enough that it does not obstruct other blood lines or dialysate lines of the dialysis system 100. For example, the temperature sensor housing 116 is typically designed to occupy an area of about 0.35 square inch to about 4.0 square inches (e.g., about 3.8 square inches) on the face of the dialysis machine 102. However, the temperature sensor housing 116 can be provided in various other sizes depending on the size and arrangement of the dialysis machine with which it is to be used.

The temperature sensor housing 116 is typically connected to the dialysis machine 102 using fasteners such as machine screws or rivets. However, other types of mechanical connections, such as snap-in or press fit connections can alternatively or additionally be used.

In some implementations, the temperature sensor housing 116 is formed of a plastic material, such as PVC, polyethylene, polypropylene, polystyrene, and/or high density polyethylene. Alternatively or additionally, the temperature sensor housing 116 can be formed of a metallic material, such as stainless steel, aluminum, nickel, tin and/or alloys of these metallic materials.

The ambient air temperature sensor 120 is located on the outer surface of the temperature sensor housing 116. The ambient air temperature sensor 120 is typically a digital temperature sensor electrically connected to the dialysis machine control unit 106 to provide the temperature of the air surrounding a section of blood line tubing to the dialysis system control unit 106. For example, the TMP06 model ambient air temperature sensor from Analog Devices, or the LM92 model ambient air temperature sensor from National Semiconductor, can be used.

The ambient air temperature sensor 120 is typically attached to the temperature sensor housing 116 by a snap-in or press fit style joint. Alternatively or additionally, the ambient air temperature sensor 120 can be attached to the housing 116 by a threaded connection, adhesives, or it can be molded into the housing during manufacturing.

The non-invasive blood temperature sensor 118 is located within the tubing slot 122 of the temperature sensor housing 116 such that it slightly protrudes from the rear inner surface of the portion of the housing 116 that forms the tubing slot 122 to measure the temperature of blood inside a section of blood line tubing. The non-invasive blood temperature sensor 118 is an infrared temperature sensor that measures the temperature of blood through a portion of blood line tubing as it flows back to the patient 124. For example, the MLX90614 Infra Red thermometer (available from Melexis Microelectronic Integrated Systems) is an infrared temperature sensor that can be used.

The non-invasive blood temperature sensor 118 is electrically connected to the dialysis machine control unit 106 such that the control unit 106 can monitor the blood temperature as required for operation of the dialysis system 100.

The non-invasive blood temperature sensor 118 is typically attached to a hole in the slot 122 of the temperature sensor housing 116 using a snap-in or press fit style joint. Alternatively or additionally, the non-invasive blood temperature sensor 118 can be attached to the temperature sensor housing 116 by a threaded connection, adhesives, or it can be molded into the housing during manufacturing.

Figure 3:
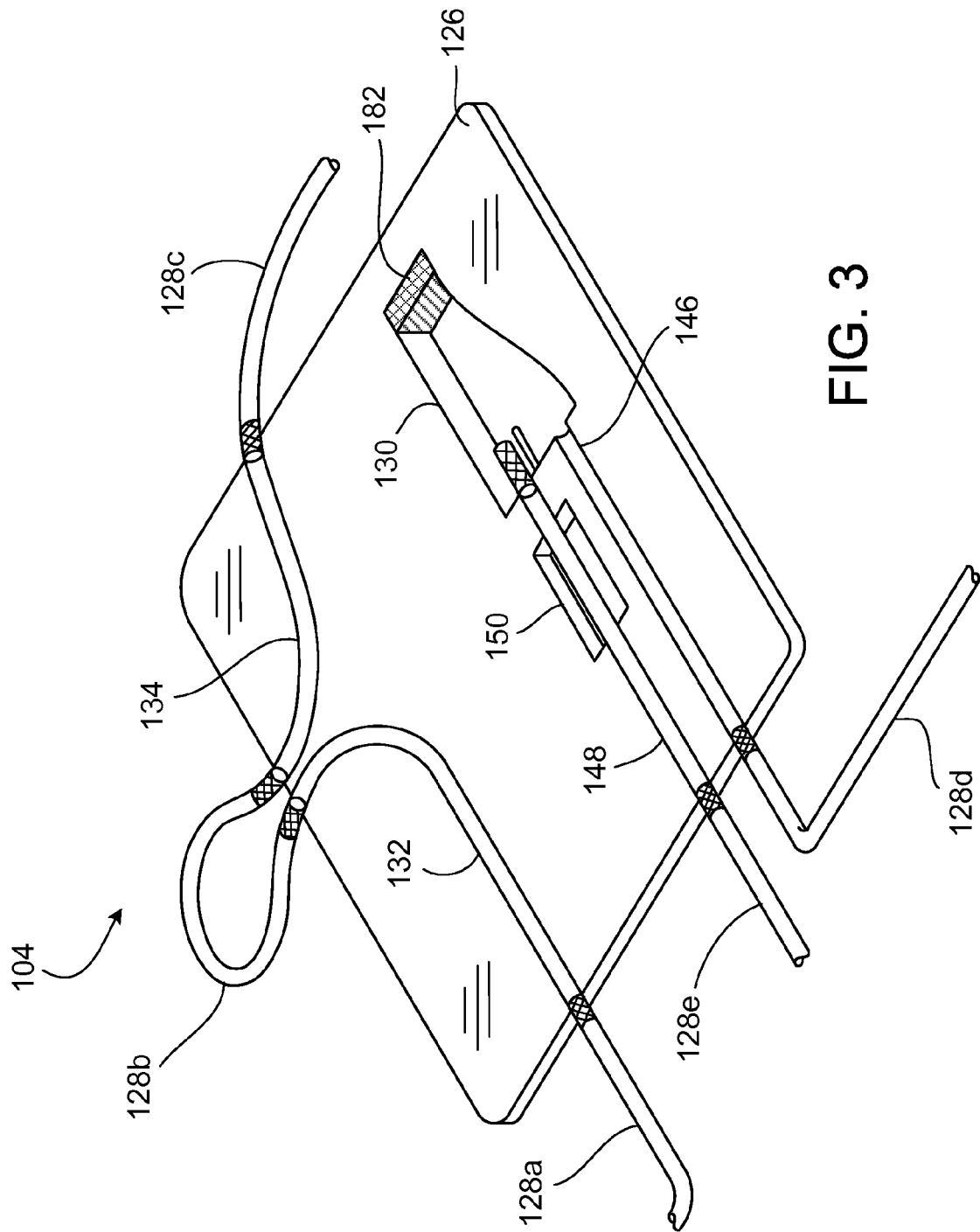
FIG. 3 is a perspective view of the blood line set of FIG. 1.

As shown in FIG. 3, the disposable blood line set 104 includes a rigid body 126, arterial tubing portions 128a-128c that provide blood to the dialyzer 136 (shown in FIG. 1), venous tubing portions 128d-128e that provide blood from the dialyzer 136 to the patient, and an air release chamber 130.

The rigid body 126 has a substantially flat surface with one or more recessed channels protruding from a front surface of the body. In some implementations, the rigid body 126 is formed of PVC, polyethylene, polypropylene, polystyrene, and/or high density polyethylene. The recessed channels can have a diameter equal to or slightly less than the diameters of the tubing portions so that the tubing portions are retained within the channels with a friction fit. The rigid body 126 has a first arterial tubing channel 132 that contains a pre-pump arterial tubing portion 128a that is connected to the patient during use to provide blood from the patient to the dialysis system 100. The pre-pump arterial tubing portion 128a exits the first arterial tubing channel 132 to form a looped blood pump arterial tubing portion 128b that is sized to fit into the raceway of peristaltic pump 108 discussed above. After the looped blood pump arterial tubing portion 128b exits the peristaltic pump 108, the post pump arterial tubing portion 128c is disposed in a second arterial tubing channel 134 of the rigid body 126, as shown. The post pump arterial tubing portion 128c then exits the second arterial tubing channel 134 to connect to and pump the patient's blood through the dialyzer (not shown).

Figure 4:
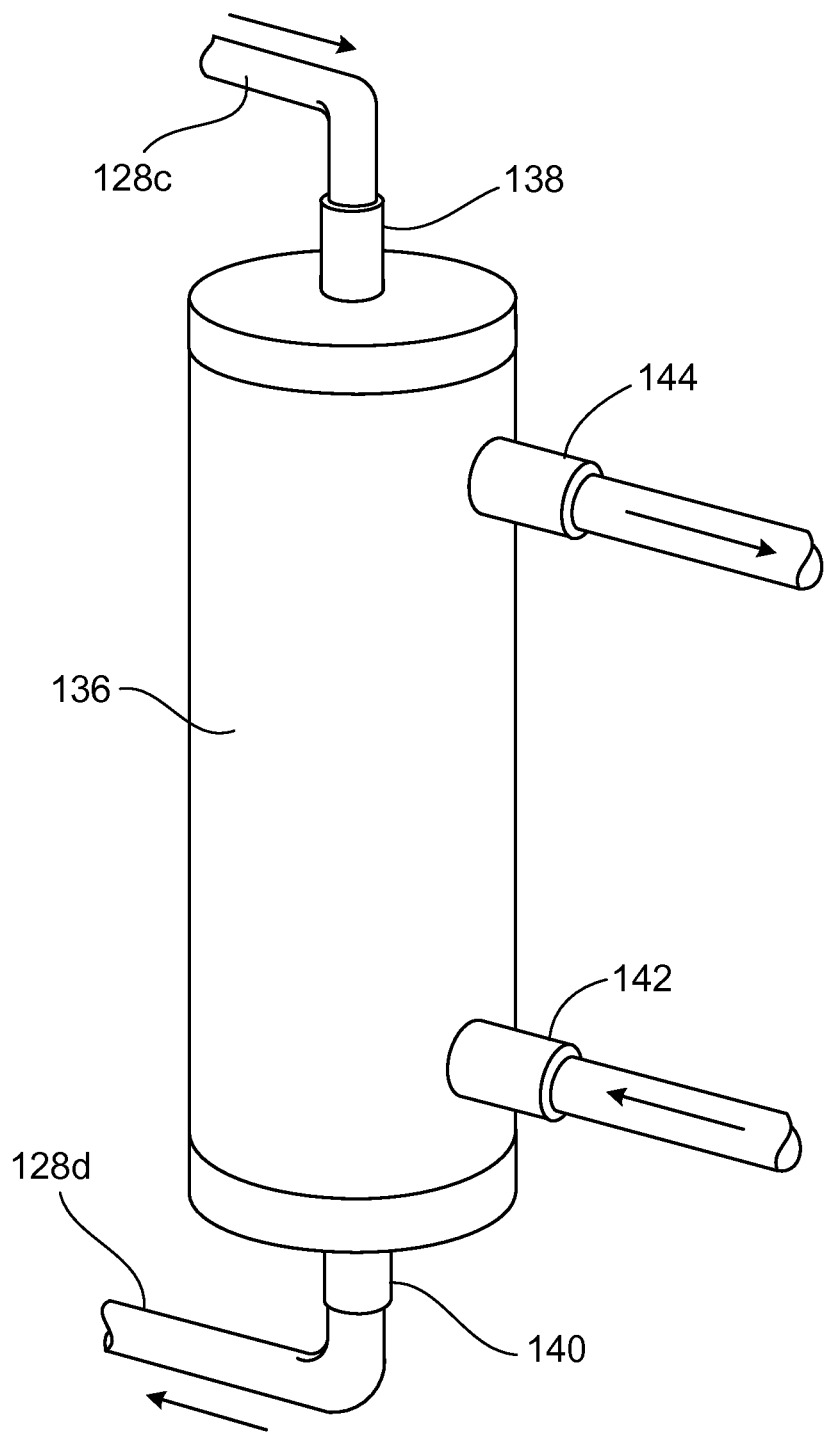
FIG. 4 is a perspective view of a dialyzer and associated tubing of the blood line set of FIG. 1.

Briefly referring to FIG. 4, the dialyzer 136 has a blood input nozzle 138 and a blood output nozzle 140 for blood to enter and exit the dialyzer 136. Temperature controlled, fresh dialysate is provided to the dialyzer 136 through a dialysate input nozzle 142 and exits through a dialysate output nozzle 144. As the dialysate flows through the dialyzer 136 it is separated from the blood by a semi-permeable membrane (e.g. semi-permeable microtubes) that allows wastes or toxins in the blood to pass through the membrane to be absorbed by the dialysate, filtering the blood.

Referring back to FIG. 3, a first venous tubing portion 128d is disposed in a first venous tubing channel 146 of the rigid body 126 to provide blood from the dialyzer to a vented air release chamber 130 that is disposed in a recessed portion of the rigid body 126. Inside the air release chamber 130, gas (e.g., air) from the blood can escape through the vent 182 before the blood continues to the patient 124. During treatment, should air be present in the blood, the blood with air bubbles flows into the air release chamber 130 through a portion the bottom of the air release chamber 130. The upper motion of the blood is impeded by gravity, while the air continues to the top of the chamber 130 where it is vented out to the atmosphere through a vent assembly 182.

A second venous tubing portion 128e is disposed in a second venous tubing channel 148 of the rigid body 126 to provide blood from the air release chamber 130 to the patient. There is an opening 150 in the rigid body 126 close to the air release chamber 130 such that when blood line set 104 is attached to the dialysis machine 102, the temperature sensor assembly 110 (shown in FIG. 2) protrudes through the opening 150 so that a portion of the second venous tubing portion 128e can be inserted into the tubing slot 122.

When the second venous tubing portion 128e is disposed in the tubing slot 122 as discussed above, the dialysis system 100 can monitor the temperature of blood that is provided back to the patient 124. However as discussed above, the non-invasive blood temperature sensor 118 measures the temperature of blood through the venous tubing wall and in the presence of ambient air, and thus the temperature measurement can be affected by the material properties of the tubing and the ambient air temperature.

The blood line tubing typically has an inner diameter of about 0.150 inch to about 0.200 inch (e.g., about 0.168 inch or about 0.1875 inch) and an outer diameter of about 0.250 inch to about 0.300 inch (e.g., about 0.285 inch). The tubing can be formed of any of various different medical grade materials. Examples of such materials include PVC, polyethylene, polypropylene, silicone, polyurethane, high density polyethylene, nylon, ABS, acrylic, isoplast, polyisoprene, and polycarbonate.

Referring back to FIG. 1, during hemodialysis treatment, blood is removed from a patient 124 and circulated through the blood line set 104 in the manner described above to remove waste from the blood. On the arterial side of the extracorporeal fluid circuit, blood flows from the patient through the arterial tubing 128a-128c. The peristaltic pump 108 pumps the blood through the arterial tubing 128a-128c to the dialyzer 136. As the blood flows through the dialyzer 136 in one direction, dialysate is pumped through the dialyzer 136 in an opposite direction to the blood flow. During this process, toxins pass through a semi-permeable surface (e.g., semi-permeable micro tubes) of the dialyzer 136, from the blood to the dialysate. As a result, the blood is filtered. As the blood and dialysate pass by each other they exchange heat, so the temperature of the blood is affected by the temperature of the dialysate. Accordingly, the temperature of the blood can be controlled by controlling the temperature of dialysate provided to the dialyzer 136. Typically, the dialysate flowing through the dialyzer 136 is maintained at a temperature of about 35° C. to about 39° C. (e.g., about 37° C.), depending on various factors, including the ambient air temperature. Typically, the blood is maintained at a temperature of about 36° C. to about 38° C. by controlling the temperature of the dialysate. However, the desired venous blood temperature is typically determined by the temperature of arterial blood that is removed from the patient, in an attempt to provide venous blood back to the patient that is as close to the temperature of the arterial blood as possible.

As discussed above, the dialysis system is equipped to monitor the temperature of blood provided to the patient during treatment. In particular, a portion of the second venous tubing portion 128e, which carries blood from the air release chamber 130 to the patient 124, is disposed in the tubing slot 122 of the temperature sensor housing 116 so that the in-line, non-invasive temperature sensor 118 can measure the temperature of blood provided to the patient 124. The measured temperature readings are then transmitted from the temperature sensor 118 to the control unit 106. If the dialysis machine control unit 106 determines that the blood provided to the patient 124 is not within a desired temperature range (e.g., within 0.10° C. to 0.5° C., within 0.2° C.) of the blood removed from the patient, the dialysis system 100 adjusts the temperature of dialysate, which results in an adjustment to the temperature of the blood provided to the patient 124. However, the non-invasive infrared temperature sensor 118 that is used to measure the temperature of the blood may provide skewed temperature readings due to the ambient air temperature and the venous tubing properties. Therefore, to more accurately control the temperature of the blood provided to the patient 124 during dialysis treatment, the in-line blood temperature measurement can be corrected based on the ambient air temperature sensor measurement and the properties of the venous tubing, and the corrected blood temperature can be used by the control unit 106 to adjust the temperature of the dialysate if desired.

During treatment, the temperature sensor assembly 110 measures the in-line blood temperature using the non-invasive temperature sensor 118 and the ambient air temperature using the ambient air temperature sensor 120. Using these two different temperature measurements, the dialysis machine control unit 106 can more accurately determine or predict the blood temperature. To do so, the dialysis machine control unit 106 accesses a look-up table that contains corrected blood temperatures based on the ambient air temperature measurement and the non-invasive blood temperature measurement for a given type of tubing (i.e., tubing having the same dimensional and material makeup of the tubing used for the second venous tubing portion 128e of the blood line set 104 to be used for a particular treatment). As shown in FIG. 5, the look-up table 152 has ambient air temperature measurements 154 along the top row and non-invasive blood temperature measurements 156 along the left column for the given tubing. The rest of the look-up table is populated with corrected blood temperature readings 158 for each of the ambient air temperature and non-invasive blood temperature combinations. The values provided in the look-up table illustrated in FIG. 5 are provided as examples only and are not intended to reflect actual values or patterns that would typically be used. If the temperature measurements from either of the ambient air temperature sensor or the non-invasive blood temperature sensor provided to dialysis system are not on the look-up table, the dialysis system 100 (e.g., the control unit 106 of the dialysis machine 102) can implement linear interpolation or similar numerical methods to estimate a corrected blood temperature based on the closest temperature intervals provided on the look-up table.

The appropriate corrected blood temperature reading 158 is then used by the dialysis system 100 to help ensure that the blood circulated through the blood line set 104 is maintained within a desired temperature range thereby providing a more comfortable experience for the patient 124.

In addition, the dialysis machine control unit 106 can use the corrected blood temperature reading 158 for other processes that utilize blood temperature information. For example, in an alternative type of blood temperature control, venous blood may be provided back to the patient at a temperature that is intentionally at a different temperature than the arterial blood taken from the patient. During this type of treatment, as arterial blood is removed from the patient, the dialysis system changes the temperature of the blood and provides venous blood to the patient at the different temperature. The dialysis system then continues to monitor the temperature of arterial blood coming from the patient to detect changes that would indicate proper blood circulation at the blood access site. In this type of blood temperature monitoring, a more accurate blood temperature measurement is also desired.

A method of populating the look-up table discussed above will now be described with respect to FIG. 6. In order to populate the look-up table with corrected blood temperatures, a series of experiments is performed to empirically determine the effect of ambient air temperature on non-invasive blood temperature measurements for a given type of tubing. Corrected temperatures are determined by attaching a substitute blood line set 160 to the dialysis machine to simulate a dialysis system and treatment under various conditions. A test fluid reservoir 162 and a temperature control unit 164 provides a test fluid (e.g., water, blood, or a blood substitute) 166 to the substitute blood line set 160 such that the test fluid 166 passes through a portion of the tubing disposed in the slot 122 of the temperature sensor assembly 110 during testing, as blood does during use of the dialysis system. The substitute blood line set 160 is generally the same as a blood line set to be used during treatment except that the substitute blood line set 160 typically does not include an air release chamber or a dialyzer.

Figure 6:
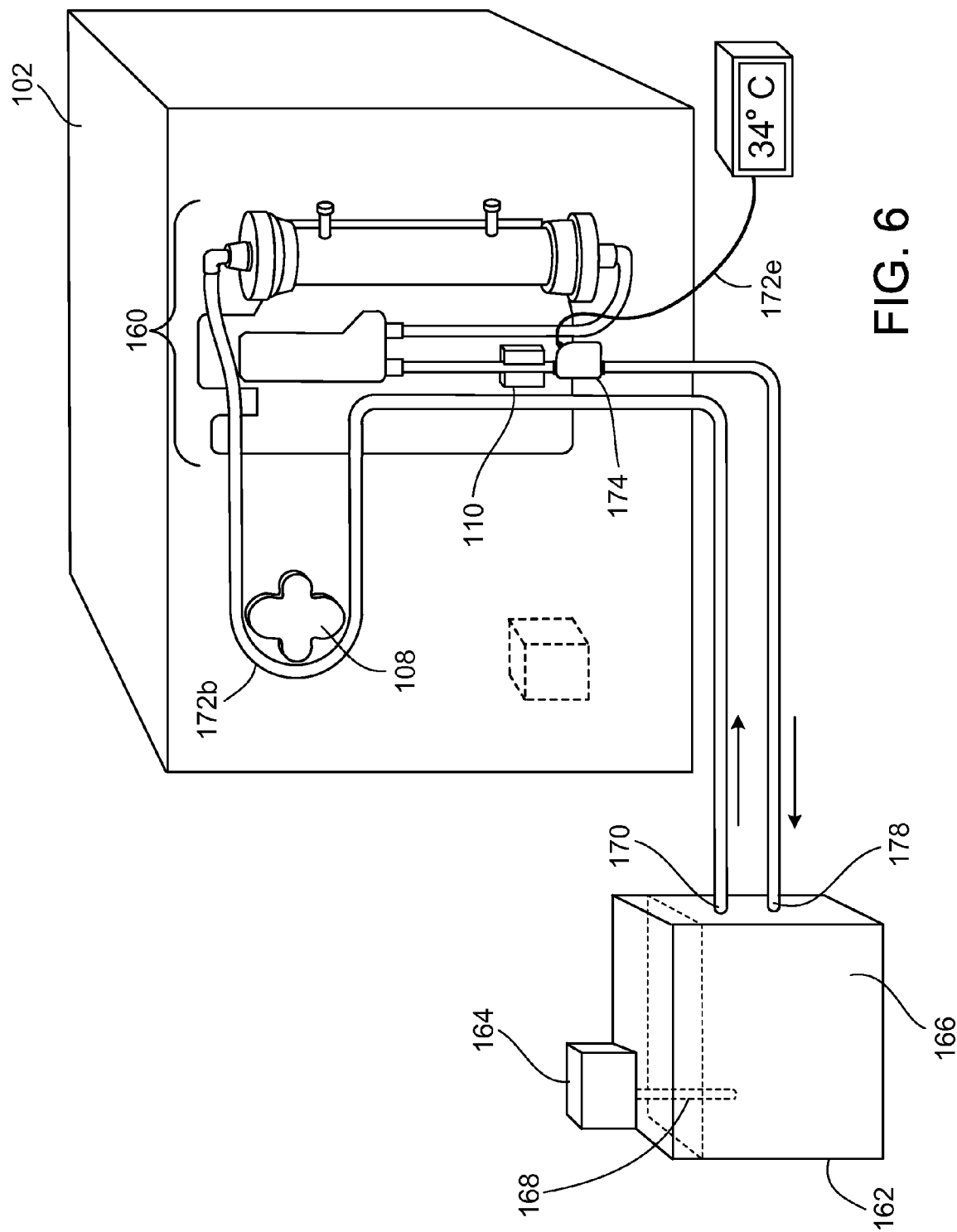
FIG. 6 is a perspective view of a test system that can be used to determine corrected blood temperatures at multiple different ambient air temperatures for a given type of blood tubing.

Still referring to FIG. 6, the temperature control unit 164 has a heating element 168 and includes a thermostat that can be controlled to maintain the temperature of the test fluid 166 contained in the test fluid reservoir 162. The test fluid reservoir outlet nozzle 170 connects to substitute arterial tubing, which allows test fluid 166 to flow from the test fluid reservoir 162 and through the substitute blood line set 160.

The substitute arterial tubing has a looped portion 172b that engages the peristaltic pump 108 of the dialysis machine 102 to permit the pump 108 to circulate the test fluid 166 through the substitute blood line set 160. A portion of substitute venous tubing 172e is disposed in the tubing slot 122 for measuring the temperature of the test fluid flowing therethrough. The tubing used in the substitute blood line set is the same type of tubing (e.g., tubing having the same dimensional and material makeup) that is used in the blood line set during treatment, so that the corrected temperatures provided in the look-up table properly take into account the type of tubing that is used in a particular treatment. If multiple different types of tubing can be used with the dialysis machine 102 (e.g., for multiple different types of treatment, such as adult dialysis, pediatric dialysis, etc.), this testing sequence is performed for each type of tubing to ensure proper temperature correction values are provided.

The substitute blood line set 160 includes an invasive, in-line temperature sensor 174, such as a Mesa 90XL meter available from Mesa Labs, that is positioned in line with the substitute venous tubing downstream of the temperature sensor assembly 110. The invasive, in-line temperature sensor 174 is typically positioned close to the non-invasive blood temperature sensor 118 so as to reduce the likelihood of the actual blood temperature changing between the invasive, in-line temperature sensor 174 and the non-invasive blood temperature sensor 118. In some implementations, for example, the invasive, in-line temperature sensor 174 is positioned within 7.0 inches (e.g., within 5 inches) of the non-invasive blood temperature sensor 118.

Figure 7:
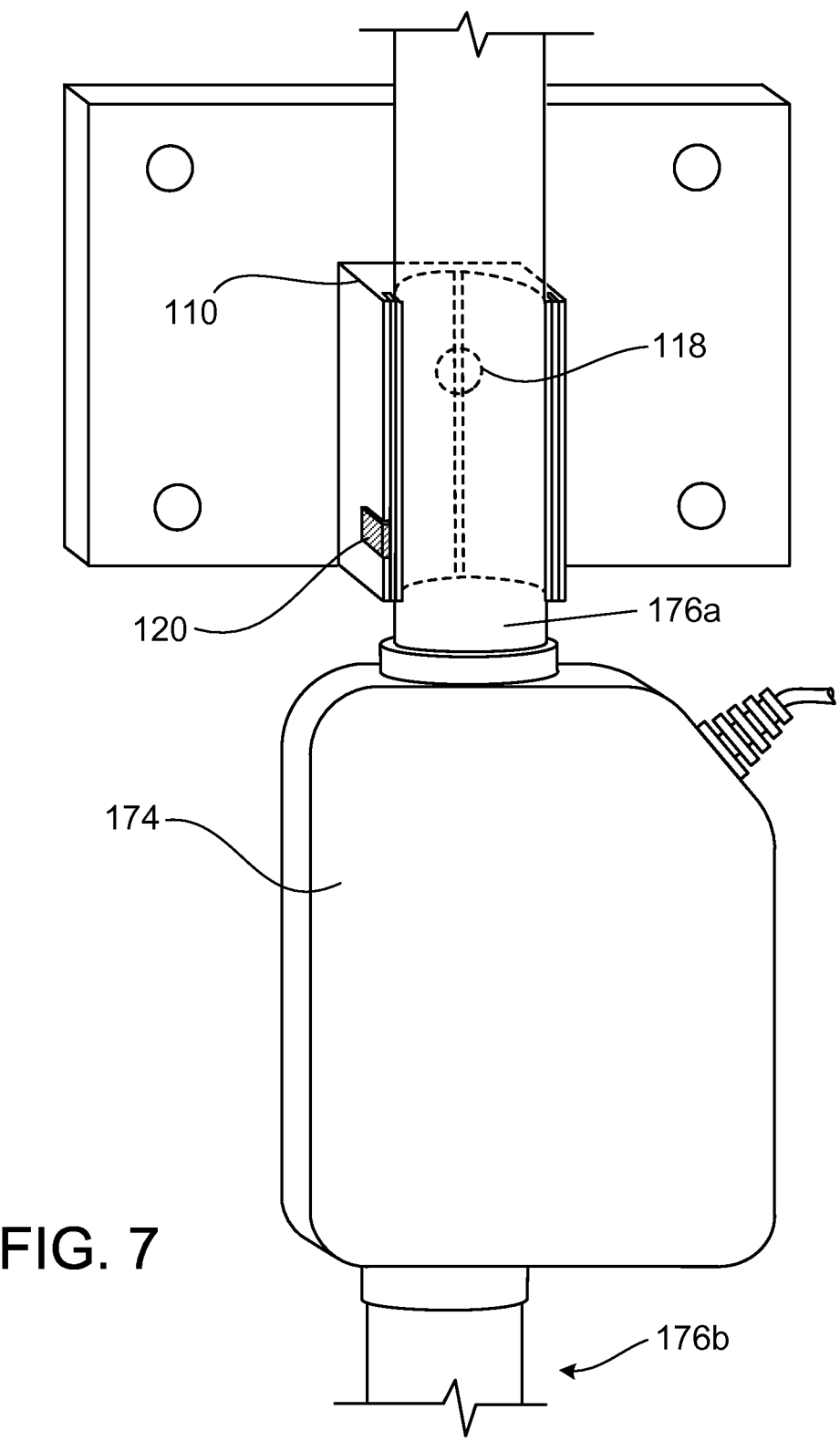
FIG. 7 is a perspective view of a venous tubing portion of a substitute blood line set of the test system of FIG. 6. The illustrated venous tubing portion is connected to the blood temperature sensor assembly of the dialysis machine, which, in this case, is part of the test system.
Figure 8:
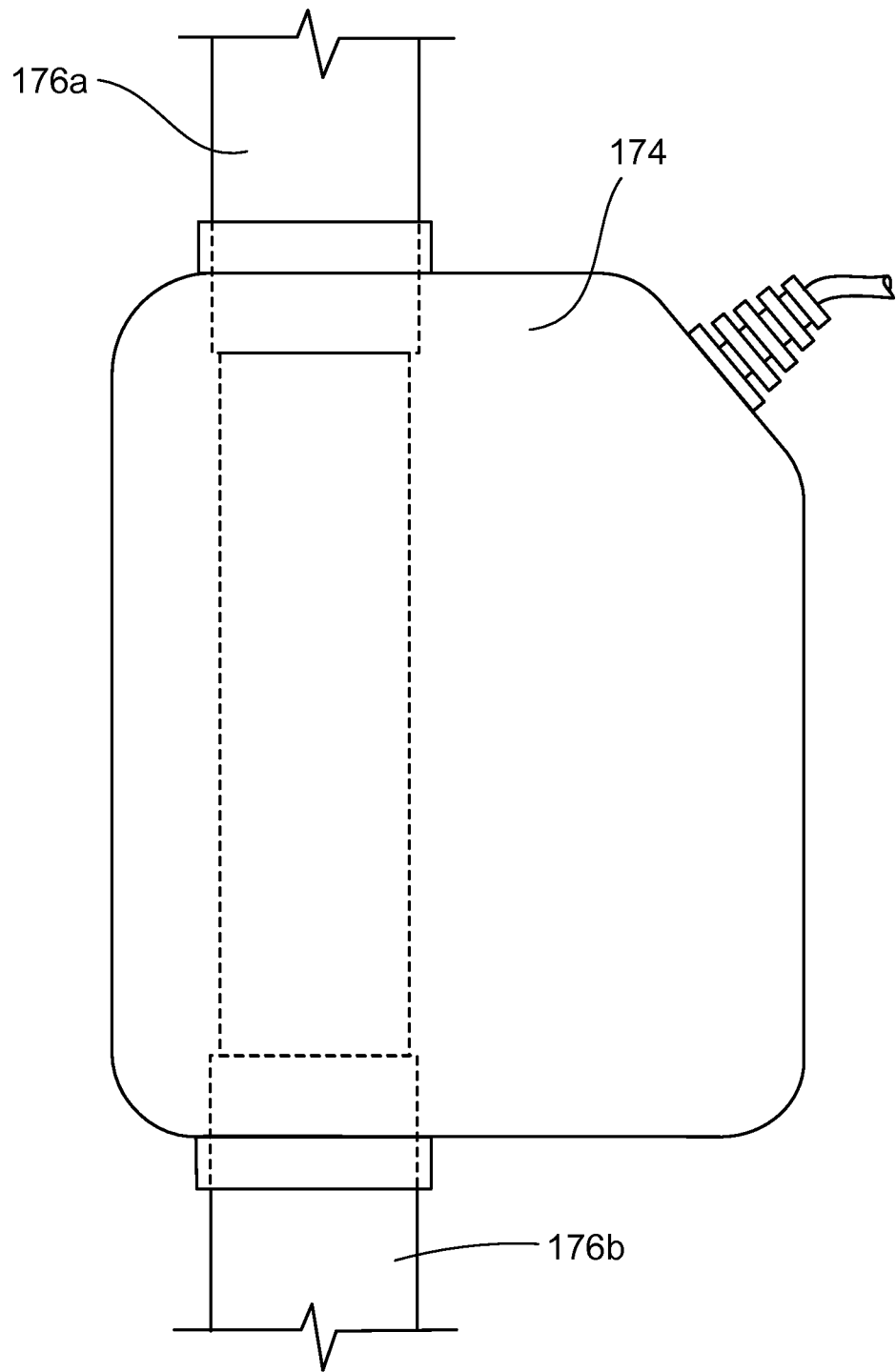
FIG. 8 is a perspective view of a venous tubing portion of the substitute blood line set of the test system of FIG. 6, showing connections between the tubing and an invasive, in-line temperature sensor.

Referring to FIGS. 7 and 8, a first substitute venous tubing portion end 176a is inserted into one end of the sensor 174, and a second substitute venous tubing portion end 176b is inserted into the other end of sensor which provides test fluid 166 to a test fluid reservoir inlet nozzle 178. The sensor 174 is typically equipped with quick-connect style couplings that allow the tubing portions to engage the sensor via a friction fit or press fit. In some implementations, threaded connections are additionally or alternatively used attach the tubing to the sensor 174.

Referring again to FIG. 6, to operate the test system, the test fluid 166 is pumped through the test system. In some implementations, the test fluid 166 is pumped at a high enough flow rate to ensure that any temperature difference based upon the distance between the non-invasive temperature sensor measurement and the invasive temperature sensor measurement would be negligible. It is believed that 500 ml/min is a sufficient flow rate for tubing having an inside diameter of 3/16 inch or less. As test fluid 166 is pumped through the substitute blood line set 160, the ambient air temperature is controlled and maintained by the room air temperature system. As the ambient temperature is maintained at a particular temperature, (e.g., 15° C.), the system is allowed to reach a steady state temperature and flow condition. In the steady state condition, the fluid temperature and flow conditions stabilize and no longer change with respect to time. Once the steady state temperature and flow condition has been achieved, the temperature measurements from the ambient air temperature sensor 120, the in-line invasive temperature sensor 174, and the in-line, non-invasive fluid temperature sensor 118 are monitored and recorded. A series of measurements (e.g., about 4-6 measurements) can be taken over a period of time with the system under steady state temperature and flow conditions. Taking a series of measurements can reduce the likelihood of obtaining an inaccurate measurement due to any anomalies in the testing equipment or the testing sequence. The series of measurements can be averaged or combined using statistical analysis to obtain a proper measurement that is representative of the system. After all temperature data from the sensors has been recorded, the temperature of the test fluid 166 is increased by a particular temperature interval, (e.g., 1° C.), the system is allowed to reach a steady state, and all temperature measurements are again recorded. This process is repeated as the temperature of the fluid is increased across a typical operational temperature range, (e.g., 33° C.-43° C.), recording all temperatures at each fluid temperature interval.

Once temperature data has been collected for the entire fluid temperature range desired, the ambient air temperature is increased by an interval (e.g., 1° C.), the fluid temperature is reduced to the initial starting temperature (e.g., 33° C.), and the test is repeated at the newly elevated ambient air temperature. This process is repeated for all desired operational ranges of fluid temperature and ambient air temperature, (e.g., 33° C.-43° C. and 15° C.-38° C., respectively), to collect all data desired.

A look-up table like the look-up table 152 discussed above is compiled from the test data for all of the tests performed. This look-up table can be loaded into the dialysis machine control unit 106. The control unit 106 is configured such that during treatment the control unit 106 can access the table, and using an ambient air temperature measurement and a non-invasive blood temperature measurement, the dialysis system 100 can determine a more accurate blood temperature measurement to be used by the system.

While certain implementations have been described, other implementations are possible.

Although the temperature sensor assembly 110 has been described as being attached to the dialysis machine 102 using a mechanical connector, the temperature sensor assembly can alternatively or additionally be attached in another manner. For example, the temperature sensor assembly can be attached using adhesives or thermal bonding techniques.

Although the temperature sensor assembly 110 has been described as being a component separate from the dialysis machine 102, in some implementations, the temperature sensor assembly can alternatively or additionally be a built-in component of the dialysis machine. For example, the housing of the temperature sensor assembly can be molded or otherwise formed onto the face of the dialysis machine.

Figure 9:
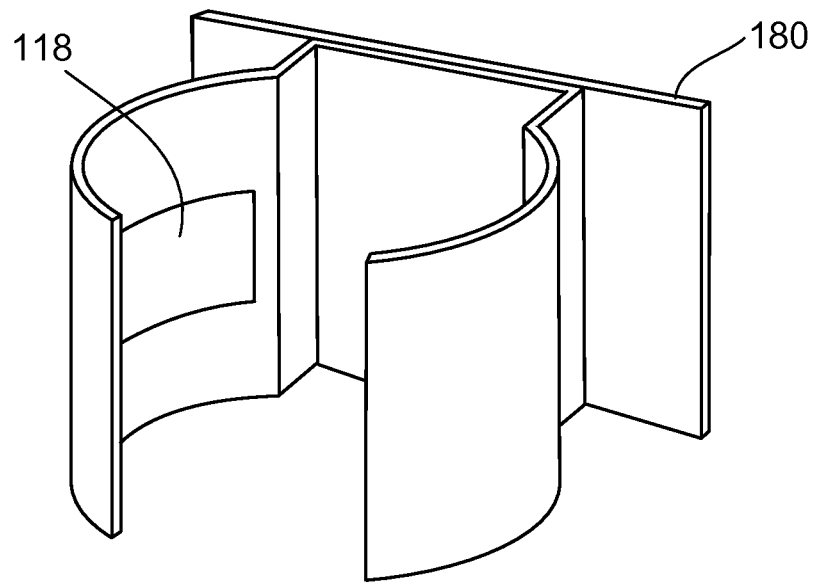
FIGS. 9 and 10 are perspective views of another type of temperature sensor assembly that can be used with the dialysis machine of FIG. 1.
Figure 10:
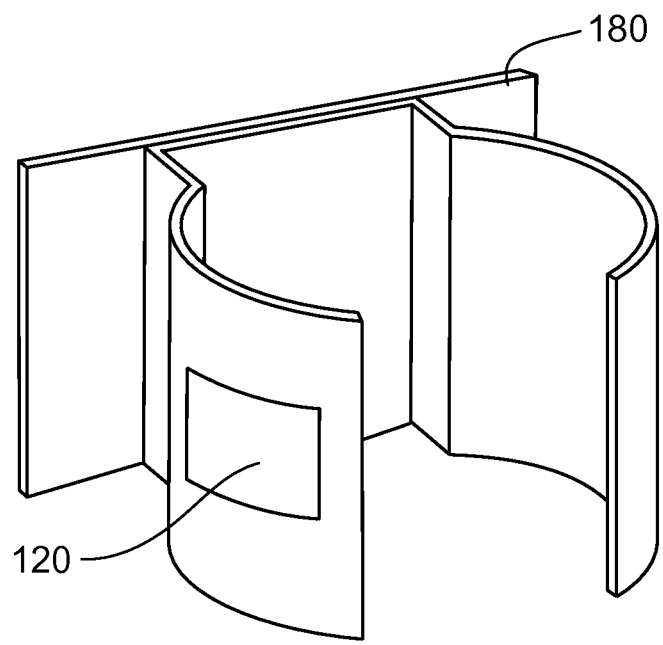

Although the temperature sensor assembly 110 has been described as including a solid body housing that forms the tubing slot 122, in some implementations, the temperature sensor assembly is formed as a resilient clip. For example, as shown in FIG. 9 and FIG. 10, a temperature sensor assembly 180 includes a clip shaped temperature sensor housing with one arm including the non-invasive temperature sensor 118 mounted to its inner surface (i.e., the surface facing the blood tube) to measure the temperature of blood in an inserted blood tube and the ambient air temperature sensor 120 on its opposite, outward facing surface.

Although the temperature sensor assemblies 110 and 180 have been described as including the ambient air temperature sensor 120 on an outer surface of the housing and the in-line blood temperature sensor 118 in the tubing slot, in some implementations, the temperature sensors are integrated into a singular sensor device mounted in a location where the air temperature sensor and the blood temperature sensor are positioned such that they can measure the ambient air temperature and the in-line blood temperature, respectively. For example, the singular sensor device can be mounted along an outer edge of the tubing slot so that it is exposed to the ambient air, but is also in a position to detect in-line blood temperature. In such an implementation, the singular sensor device is electrically connected to the dialysis machine with one wiring harness which connects both temperature sensors. Additionally, such an arrangement can reduce the number of openings and mounting devices required to mount temperature sensors to the temperature sensor assembly that would otherwise be needed to mount multiple temperature sensors.

Although the ambient air temperature sensor 120 has been described as being a digital temperature sensor, in some implementations, the ambient air sensor can be another type of temperature sensor. For example, the ambient air temperature sensor can be a thermistor. Alternatively, the ambient air temperature sensor can be any of various other types of temperature sensors, including thermocouples.

While the non-invasive blood temperature sensor and the ambient air temperature sensor have been described as being mounted to a single housing, other arrangements are possible. For example, the ambient air temperature can be positioned on a portion of the dialysis machine that is separate from the housing the temperature sensor assembly. In some implementations, the ambient air temperature sensor is entirely separate from the dialysis machine. In such implementations, the ambient air temperature sensor and the dialysis machine (e.g., the control unit of the dialysis machine) are connected (e.g., by hard wire or wirelessly) so that data can be transmitted from the ambient air temperature sensor to the dialysis machine.

Although the rigid body 126 of the blood line set 104 has been described as having recessed channels to secure the blood lines to the rigid body 126, the blood lines can alternatively or additionally be secured by any of various other techniques. For example, mechanical attachment devices (e.g., clips or clamps) can be attached to the rigid body 126 and used to retain the lines. As another example, the lines can be adhered to or thermally bonded to the rigid body 126.

In some implementations, the hemodialysis machine 102 includes pressure sensors to monitor the blood pressure in the system. In such implementations, the rigid body 126 of the blood line set 104 typically includes additional apertures to allow the blood lines to contact the pressure sensors on the face of the machine.

Although the in-line invasive temperature sensor 174 has been described as a temperature sensor device in which tubing is inserted into both ends so that fluid can flow through the sensor device, other types of sensors can be used. Examples of other suitable types of sensors include a thermocouple or a thermistor inserted into a portion of blood line tubing.

Although testing for corrected blood temperature measurements has been described as using an actual dialysis machine, in some implementations, a non-dialysis machine testing unit can be used. For example, a testing unit configured substantially only to pump test fluid and measure temperatures, including a peristaltic pump, a temperature sensor assembly, and a control unit can be used.

Although the ambient air temperature during testing has been described as 15° C.-38° C., the ambient air temperature range can be larger or smaller depending on the expected environment where the device will be used. In some implementations, the ambient air temperature range used for testing is 10° C.-40° C. In other implementations, the ambient air temperature range used for testing is 20° C.-35° C.

Although the test fluid temperature range during testing has been described as 33° C.-43° C., in some implementations, the test fluid temperature range is higher or lower depending on the expected blood temperatures to be encountered or maintained during treatment. In some implementations, for example, the test fluid temperature range is 30° C.-46° C.

Although the test sequence to determine corrected temperatures has been described as allowing the fluid temperature to decrease to the lowest test temperature and then conducting the test by ramping the temperature up, the sequence could vary as long as data is collected for the entire range of both the ambient air temperature and test fluid temperature. For example, once the highest test fluid temperature has been reached and the data is collected, the ambient air temperature can be changed to the next interval and data can be collected at each fluid temperature interval as the test fluid temperature is reduced, recording data at each of the test fluid temperature intervals.

While the substitute blood line set 160 has been described as a tubing set that does not include certain components found in the blood line set 104, other types of substitute blood line sets can be used. In certain implementations, for example, the substitute blood line set is simply a version of the blood line set 104 that has been modified to include an invasive, in-line blood temperature sensor.

Although correcting the blood temperature measurements has been described as accessing a look-up table which provides the corrected temperature, the dialysis control unit can alternatively or additionally include a system of equations to calculate a corrected blood temperature based on given measured blood temperature and ambient air temperature. For example, instead of using the test data discussed above to populate a table of corrected temperatures, the test data can be manipulated using common numerical method techniques to obtain a system of equations where the ambient air temperature measurement and the non-invasive blood temperature measurement are inputs and corrected blood temperature is the output. Common computer programs, such as Microsoft Excel, have been shown suitable to create a polynomial equation to estimate corrected blood temperature by plotting the test results and using a trendline function to create an equation to represent the data. As discussed above, since the type of tubing used affects the non-invasive temperature measurements, there would be particular equations for particular tubing types.

Although the dialysis system 100 has been described as using the dialysis machine control unit 106 to determine corrected blood temperature measurements, in some implementations, a separate control unit is used to determine a corrected in-line blood temperature measurement. For example, the dialysis system can include a separate temperature measurement control unit that is electrically connected to the ambient air temperature sensor 120 and the non-invasive blood temperature sensor 118, and the control unit can contain and process the look-up table 152 or equations to correct the blood temperature measurement. The temperature measurement control unit can be electrically connected to the dialysis machine control unit to provide corrected blood temperature measurements to the dialysis system.

While the temperature sensor assemblies 110, 180 have been described as being used in dialysis systems, the sensor assemblies 110, 180 can be used in other types of blood treatment and processing systems, such as cardio pulmonary by-pass systems, blood transfusion systems, apheresis and plasmapheresis.

While the temperature sensor assemblies discussed above have been described as being used in various different types of blood-treatment systems, in some cases, the sensor assemblies can be used to determine corrected temperature values of other types of medical fluids. In certain implementations, for example, the temperature sensor assemblies are used in peritoneal dialysis systems to determine corrected temperature values of dialysis flowing to and/or from a patient. In such implementations, the blood temperature sensor assemblies are connected to a dialysate line in much the same way as they are described above as being connected to the blood lines.

Other embodiments are within the scope of the following claims.

What is claimed is:

1. A medical fluid pumping system comprising:
a medical fluid pumping machine comprising a pump;
fluid circuitry comprising tubing that can be connected to the pump in a manner such that the pump can move a medical fluid through the tubing of the fluid circuitry; and
a sensor assembly comprising:
a housing defining a slot to retain a portion of tubing of the fluid circuitry;
a non-invasive fluid temperature sensor mounted to the housing and configured to detect a temperature of medical fluid in the portion of tubing of the fluid circuitry when the portion of tubing is disposed in the slot and the medical fluid is flowing through the portion of tubing; and
an ambient air temperature sensor mounted to the housing;
wherein the medical fluid pumping machine comprises a control unit that is in communication with the non-invasive fluid temperature sensor and the ambient air temperature sensor; wherein the control unit comprises a look-up table that provides a corrected medical fluid temperature for each of multiple different combinations of temperatures of medical fluid detected by the non-invasive fluid temperature sensor and temperatures of ambient air detected by the ambient air temperature sensor.

2. The medical fluid pumping system of claim 1, wherein the medical fluid pumping machine is a dialysis machine.

3. The medical fluid pumping system of claim 2, wherein the medical fluid is blood.

4. The medical fluid pumping system of claim 1, wherein the control unit comprises an equation to obtain a corrected medical fluid temperature based on a temperature of medical fluid detected by the non-invasive fluid temperature sensor and a temperature of ambient air detected by the ambient air temperature sensor.

5. The medical fluid pumping system of claim 1, wherein the control unit is adapted to run a statistical analysis to obtain a corrected medical fluid temperature based on a temperature of medical fluid detected by the non-invasive fluid temperature sensor and a temperature of ambient air detected by the ambient air temperature sensor.

6. The medical fluid pumping system of claim 1, wherein the ambient air temperature sensor is mounted to an outer surface of the housing.

7. The medical fluid pumping system of claim 6, wherein the non-invasive fluid temperature sensor is mounted to an inner surface of the housing such that the non-invasive fluid temperature sensor is adjacent the portion of tubing when the portion of tubing is disposed in the slot.

8. The medical fluid pumping system of claim 7, wherein the non-invasive fluid temperature sensor is positioned to contact the portion of tubing when the portion of tubing is disposed in the slot.

9. The medical fluid pumping system of claim 1, wherein the non-invasive fluid temperature sensor is positioned in the slot in the housing.

10. The medical fluid pumping system of claim 1, wherein the non-invasive fluid temperature sensor is an infrared temperature sensor.

11. The medical fluid pumping system of claim 1, wherein the fluid circuitry further comprises a drip chamber, a dialyzer system, an air release chamber, and a structural support member.

12. The medical fluid pumping system of claim 11, wherein the non-invasive fluid temperature sensor is positioned downstream of the air release chamber.

* * * * *